United States Patent [19]

Svensson et al.

[11] Patent Number: 5,866,590
[45] Date of Patent: Feb. 2, 1999

[54] PHARMACEUTICAL COMPOSITION CONTAINING TIAGABINE HYDROCHLORIDE AND THE PROCESS FOR ITS PREPARATION

[75] Inventors: Jørgen Ryhl Svensson, Frederikssund; Lars Nygaard, Valby; Tina Meinertz Andersen, Hoersholm; Helle Weibel, Hilleroed; Thyge Borup Hjorth, Farum, all of Denmark

[73] Assignee: Novo Nordisk A/S, Bagsvaerd, Denmark

[21] Appl. No.: 945,585

[22] PCT Filed: Apr. 29, 1996

[86] PCT No.: PCT/DK96/00192

§ 371 Date: Oct. 28, 1997

§ 102(e) Date: Oct. 28, 1997

[87] PCT Pub. No.: WO96/34606

PCT Pub. Date: Nov. 7, 1996

[30] Foreign Application Priority Data

May 5, 1995 [DK] Denmark ................................. 0523/95

[51] Int. Cl.⁶ ...................... A61K 31/445; A61K 31/355; A61K 31/34

[52] U.S. Cl. ........................... 514/326; 514/458; 514/474
[58] Field of Search ..................................... 514/326, 458, 514/474

[56] References Cited

U.S. PATENT DOCUMENTS

| 5,010,090 | 4/1991 | Gronvald et al. | 514/326 |
| 5,354,760 | 10/1994 | Petersen et al. | 514/326 |
| 5,591,451 | 1/1997 | Gupta et al. | 424/464 |
| 5,660,861 | 8/1997 | Joa et al. | 424/465 |

OTHER PUBLICATIONS

Weibel, H., et al., Proc. 1st World Meeting on Pharmaceutics, Biopharmaceutics and Pharmaceutical Technology – Budapest, pp. 951–952, (1995).

*Primary Examiner*—Raymond Henley, III
*Attorney, Agent, or Firm*—Steve T. Zelson, Esq.; Cheryl H. Agris, Esq.

[57] ABSTRACT

The present invention provides a new stable pharmaceutical composition containing tiagabine hydrochloride as active ingredient.

12 Claims, No Drawings

PHARMACEUTICAL COMPOSITION CONTAINING TIAGABINE HYDROCHLORIDE AND THE PROCESS FOR ITS PREPARATION

CROSS-REFERENCE TO RELATED APPLICATIONS

This application is a 35 U.S.C. 371 national application of PCT/DK96/00192 filed Apr. 29, 1996 and claims priority under 35 U.S.C. 119 of Danish application 0523/95 filed May 5, 1995, the contents of which are fully incorporated herein by reference.

The subject-matter of the present invention is a new pharmaceutical composition containing tiagabine hydrochloride as active ingredient and the process for its preparation.

In the present invention the R.isomer of N-(4,4-di(3-methylthien-2-yl)but-3-enyl-nipecotic acid is referred to by its generic name (INN): tiagabine, which is a well tolerated medication, having antiepileptic activity.

The compound N-(4,4-di(3-methylthien-2-yl)but-3-enyl-nipecotic acid is disclosed in USP 5,010,090.

Various solutions have been proposed for the preparation of medications based on tiagabine hydrochloride.

The aim of the present invention is to supply a new composition intended for the preparation of tiagabine hydrochloride with improved stability, in particular solid dosage forms thereof.

It has been found in fact that tiagabine hydrochloride decomposes in the presence of and in contact with oxygen and water.

Thus, from a first aspect, the subject-matter of the present invention is a pharmaceutical composition intended for the preparation of dosage forms and in particular solid dosage forms containing an efficacious quantity of tiagabine hydrochloride or of one of its pharmaceutically acceptable salts as active ingredient and characterised in that it contains at least one pharmaceutically acceptable antioxidant agent, in a sufficient quantity to stabilise the active ingredient.

Thus the present invention is based on the surprising discovery of the fact that the stability of tiagabine hydrochloride, or of one of its pharmaceutically acceptable salts, can be considerably improved in preparations containing tiagabine hydrochloride or of its pharmaceutically acceptable salts and antioxidant agent.

Tiagabine hydrochloride, together with a conventional adjuvant, antioxidant carrier, or diluent, and if desired a pharmaceutically acceptable acid addition salt thereof, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or as pessaries for vaginal use; or in the form of sterile injectable solutions for parenteral (including subcutaneous) use.

Within the framework of the present description and of the claims, by powders is meant any mixture of components, granulated or not, intended to be placed in solution and/or in suspension in water, or again to be ingested directly or by any other appropriate means as for example in a mixture with a food product.

In accordance with a particular characteristic of the invention, the granulation is carried out as a melt-granulation.

In accordance with another particular characteristic, this composition also contains pharmaceutically acceptable diluents.

In accordance with a particular characteristic of the invention, the antioxidant agent cited above is selected from among α-tocopherol, γ-tocopherol, δ-tocopheral, extracts of natural origin rich in tocopherol, L-ascorbic acid and its sodium or calcium salts, ascorbyl palmitate, propyl gallate (PG), octyl gallate, dodecyl gallate, butylated hydroxy anisole (BHA) and butylated hydroxy toluene (BHT).

In accordance with a currently preferred embodiment, the antioxidant agent will be α-tocopherol.

In accordance with another particular characteristic of the invention, the diluent is lactose and/or polyethylenglycol.

However, any other pharmaceutically acceptable diluents could be used.

The quantities of diluents can be easily determined by a person skilled in the art and depend of course on the final pharmaceutical form required.

Generally speaking, a composition which complies with the present invention and which are intended for the preparation of tablets, may contain, expressed in parts by weight per 100 parts of tiagabine hydrochloride, or of one of its pharmaceutically acceptable salts:

between 100 and 4000 parts by weight of anhydrous lactose;
between 1 and 100 parts by weight of an antioxidant, in the case of α-Tocopherol preferably between 1 and 50 parts by weight;
between 50 and 500 parts by weight of pregelatinized starch;
between 1000 and 10000 parts by weight of microcrystalline cellulose;
between 10 and 500 parts by weight of crospovidone;
between 10 and 500 parts by weight of silicon dioxide;
between 10 and 500 parts by weight of hydrogenated vegetable oil;
between 10 and 500 parts by weight of magnesium stearate;
between 10 and 500 parts by weight of hydroxypropyl methylcellulose;
between 10 and 500 parts by weight of hydroxypropyl cellulose;
between 1000 and 10000 parts by weight of Mannitol;
between 10 and 500 parts by weight of stearic acid;
between 10 and 500 parts by weight of Titanium Dioxide;
All excipients are of pharmaceutically acceptable grade.

In a preferred composition according to the present invention the amount of antioxidant is between 1 and 50 parts by weight per 100 parts of tiagabine hydrochloride.

In a more preferred composition according to the present invention the type of antioxidant is selected from the fat-soluble antioxidant, and in its most preferred form from α-tocopherol.

According to a preferred embodiment of the invention the water content of the excipients is very low. More specifically the water content in the diluents is very low in order to minimize the water content of the pharmaceutical composition. Lactose is used in its anhydrous form.

Furthermore, all excipients may be applied in a dry form, preferably obtained by heating the excipients before mixing, to minimize the water content of the pharmaceutical composition.

In accordance with a second aspect, the subject-matter of the present invention is a pharmaceutical preparation, in the form of tablet or powder, characterised in that it contains a composition as defined previously associated if required with at least one customary additive selected from among the sweeteners, flavouring agents, colours and lubricants.

The choice of these additives and their quantity can easily be determined by a person skilled in the art.

A preferred manufacturing process for pharmaceutical compositions according to the invention is mixing of tiagabine hydrochloride, one or more antioxidants and other pharmaceutical excipients followed by meltgranulation in a high shear mixer. Polyethylene glycols, waxes, stearic acid or other low temperature melting binders can be used. The granules can be filled into capsules, compressed into tablets or used in other pharmaceutical dosage forms.

More preferably the manufacturing process applied is direct compression of tablets, wherein tiagabine hydrochloride, one or more antioxidants and other excipients suitable for direct compression are mixed followed by tabletting.

Yet, another preferred embodiment of the manufacturing process is wet granulation, where granules are obtained by wet massing of tiagabine hydrochloride, together with one or more antioxidants and other excipients.

The most preferred process includes the melt granulation step whereby tiagabine hydrochloride is kept at conditions of low water vapor pressure.

A sweetener may be a natural sugar such as sucrose or sorbitol or a synthetic product such as saccharine or aspartame. Saccharine will be used to advantage.

When the antioxidant selected is α-tocopherol, which is hydrophobic, it can be advantageous to emulsify it in an appropriate solvent such as for example water or an organic solvent compatible with tiagabine hydrochloride.

Various emulsifying agents conventionally used in pharmacy may also be used to create this emulsion.

The present invention will be illustrated with the following non-exhaustive examples.

EXAMPLE 1

Tiagabine hydrochloride tablets stabilized with α-Tocopherol

| Tablet Strengths, mg | 8 | 8 |
|---|---|---|
| Tablet Gross Mass, mg | 320 | 320 |
| Tiagabine Hydrochloride Monohydrate | 8.35 | 8.35 |
| Polyethylene Glycol 6000, NF | 16.0 | 16.0 |
| Lactose, anhydrous, NF | 279 | 279 |
| α-Tocopherol, Ph. Eur. | 0.800 | 0 |
| Talc, Ph. Eur. | 16.0 | 16.8 |

Tiagabine hydrochloride monohydrate, α-tocopherol, polyethylene glycol 6000 and anhydrous lactose are blended in a high speed mixer and granulated by melt granulation. After cooling, the granules are blended with talc and compressed into tablets on a tabletting machine.

The stability of the tablets is improved compared to tablets without α-tocopherol. This is seen from stability studies where the extent of degradation of tiagabine hydrochloride is expressed as the total sum of degradation products. Results are shown in Table 1.

TABLE 1

Stability of Tiagabine Hydrochloride Tablets.

| | Sum of degradation products after 18 months stored at 25° C./60% RH. |
|---|---|
| Tablets with α-tocopherol | 0.5% |
| Tablets without α-tocopherol | 1.9% |

EXAMPLE 2

Tiagabine Hydrochloride Tablets stabilized with α-Tocopherol and Ascorbyl Palmitate

| Tablet Strengths, mg | 8 | 8 |
|---|---|---|
| Tablet Gross Mass, mg | 320 | 320 |
| Tiagabine Hydrochloride Monohydrate | 8.35 | 8.35 |
| Polyethylene Glycol 6000, NF | 16.0 | 16.0 |
| Lactose, anhydrous, NF | 279 | 279 |
| α-Tocopherol, Ph. Eur. | 0.400 | 0 |
| Ascorbyl Palmitate | 0.400 | 0 |
| Talc, Ph. Eur. | 16.0 | 16.8 |

Tiagabine hydrochloride monohydrate, α-tocopherol, ascorbyl palmitate, polyethylene glycol 6000 and anhydrous lactose are blended in a high speed mixer and granulated by melt granulation. After cooling, the granules are blended with talc and compressed into tablets on a tabletting machine.

EXAMPLE 3

Filmcoated Tiagabine Hydrochloride Tablets stabilized with α-Tocopherol

| Tablet Strengths, mg | 10 | 10 |
|---|---|---|
| Tablet Gross Mass, mg | 320 | 320 |
| Tiagabine Hydrochloride Monohydrate | 11.5 | 11.5 |
| Polyethylene Glycol 6000, NF | 20.0 | 20.0 |
| α-Tocopherol, Ph. Eur. | 1.10 | 0 |
| Talc, Ph. Eur. | 16.0 | 16.0 |
| Lactose, anhydrous, NF | up to 320 | up to 320 |

Tiagabine hydrochloride monohydrate, α-tocopherol, polyethylene glycol 6000 and anhydrous lactose are blended in a high speed mixer and granulated by melt granulation. After cooling, the granules are blended with talc and compressed into tablets on a tabletting machine.

In order to protect against light and improve the appearance of the tablets, the tablets are film-coated.

The tablets were coated with the following film-coating composition where an amout of coating material of 5 mg/cm² were chosen as being satisfactory with respect to stability of the tablets:

| Methylhydroxypropylcellulose Ph. Eur. | ~4.34 mg/tablet |
|---|---|
| Polyethylene Glycol 6000, NF | ~5.20 mg/tablet |
| Titanium Dioxide, Ph. Eur. | ~1.73 mg/tablet |
| Purified Water, Ph. Eur. | q.s. |
| Talc, Ph. Eur. (Added as polishing agent at the end of the film-coating process (0.5% w/w of tablet core). Absorbed amount is not quantified. | |

EXAMPLE 4

Filmcoated Tiagabine Hydrochloride Tablets stabilized with α-Tocopherol and Ascorbyl Palmitate

| Tablet Strengths, mg | 10 | 10 |
|---|---|---|
| Tablet Gross Mass, mg | 320 | 320 |
| Tiagabine Hydrochloride Monohydrate | 11.5 | 11.5 |
| Polyethylene Glycol 6000, NF | 20.0 | 20.0 |
| α-Tocopherol, Ph. Eur. | 0.55 | 0 |
| Ascorbyl Palmitate | 0.55 | 0 |
| Talc, Ph. Eur. | 16.0 | 16.0 |
| Lactose, anhydrous, NF | up to 320 | up to 320 |

Tiagabine hydrochloride monohydrate, α-tocopherol, ascorbyl palmitate, polyethylene glycol 6000 and anhydrous lactose are blended in a high speed mixer and granulated by melt granulation. After cooling, the granules are blended with talc and compressed into tablets on a tabletting machine.

In order to protect against light and improve the appearance of the tablets, the tablets are film-coated.

The tablets were coated with the following film-coating composition where an amount of coating material of 5 mg/cm$^2$ were chosen as being satisfactory with respect to stability of the tablets:

| | |
|---|---|
| Methylhydroxypropylcellulose Ph. Eur. | ~4.34 mg/tablet |
| Polyethylene Glycol 6000, NF | ~5.20 mg/tablet |
| Titanium Dioxide, Ph. Eur. | ~1.73 mg/tablet |
| Purified Water, Ph. Eur. | q.s. |
| Talc, Ph. Eur. | |
| (Added as polishing agent at the end of the film-coating process (0.5% w/w of tablet core). Absorbed amount is not quantified. | |

EXAMPLE 5

Tiagabine Hydrochloride Tablets stabilized with α-Tocopherol and Sodium Citrate as chelating agent

| Tablet Strengths, mg | 8 | 8 |
|---|---|---|
| Tablet Gross Mass, mg | 320 | 320 |
| Tiagabine Hydrochloride Monohydrate | 8.35 | 8.35 |
| Polyethylene Glycol 6000, NF | 16.0 | 16.0 |
| Lactose, anhydrous, NF | 279 | 279 |
| α-Tocopherol, Ph. Eur. | 0.400 | 0 |
| Sodium Citrate | 0.400 | 0 |
| Talc, Ph. Eur. | 16.0 | 16.8 |

Tiagabine Hydrochloride monohydrate, α-tocopherol, sodium citrate, polyethylene glycol 6000 and anhydrous lactose are blended in a high speed mixer and granulated by melt granulation. After cooling, the granules are blended with talc and compressed into tablets on a tabletting machine.

EXAMPLE 6

Tiagabine Hydrochloride Tablets stabilized with α-Tocopherol and EDTA(*) as chelating agent

| Tablet Strengths, mg | 8 | 8 |
|---|---|---|
| Tablet Gross Mass, mg | 320 | 320 |
| Tiagabine Hydrochloride Monohydrate | 8.35 | 8.35 |
| Polyethylene Glycol 6000, NF | 16.0 | 16.0 |
| Lactose, anhydrous, NF | 279 | 279 |
| α-Tocopherol, Ph. Eur. | 0.270 | 0 |
| EDTA(*) | 0.530 | 0 |
| Talc, Ph. Eur. | 16.0 | 16.8 |

(*)EDTA in its form of Disodium Edetate.

Tiagabine hydrochloride monohydrate, α-tocopherol, EDTA(*), polyethylene glycol 6000 and anhydrous lactose are blended in a high speed mixer and granulated by melt granulation. After cooling, the granules are blended with talc and compressed into tablets on a tabletting machine.

EXAMPLE 7

Solution containing tiagabine hydrochloride

| Composition: | |
|---|---|
| Tiagabine hydrochloride | 1.14 mg |
| Glucose monohydrate | 55.0 mg |
| Sodium hydroxide 2N | q.s. |
| Water | ad 1.00 ml |
| α-tocopherol | 0.250 mg |
| Na-citrate | 0.250 mg |
| Ascorbyl Palmitate | 0.250 mg |

Manufacturing method

Tiagabine hydrochloride, Na-citrate and the antioxidants are mixed in a flask with water at room temperature by stirring until the substance is soluted (approximately five minutes). Glucose monohydrate is added to the solution by stirring at room temperature for two minutes. At last the pH is adjusted to 7.4 and the solution is diluted with water.

The solution is used for administration of tiagabine hydrochloride as injection and as intravenous infusion. The formulation is also used for nasal and pulmonal delivery and as an oral solution or mixture.

EXAMPLE 8

Solution containing tiagabine hydrochloride

| Composition: | |
|---|---|
| Tiagabine hydrochloride | 1.14 mg |
| Glucose monohydrate | 55.0 mg |
| Sodium hydroxide 2N | q.s. |
| Water sterile | ad 1.00 ml |
| α-tocopherol | 0.250 mg |
| Ascorbyl Palmitate | 0.250 mg |
| EDTA (Disodium Edetate) | 0.500 mg |

Manufacturing method

Tiagabine hydrochloride, the antioxidants and chelating agent are mixed in a flask with water at room temperature by stirring until the substance is soluted (approximately five minutes). Glucose monohydrate is added to the solution by stirring at room temperature for two minutes. At last the pH is adjusted to 7.4 and the solution is diluted with water.

The solution is used for administration of tiagabine hydrochloride as injection and as intravenous infusion. The formulation is also used for nasal and pulmonal delivery and as an oral solution or mixture.

EXAMPLE 9
Gel containing tiagabine hydrochloride

| Composition: | |
|---|---|
| Tiagabine hydrochloride | 1.14 mg |
| Carbomer 940 | 5.00 mg |
| Sodium hydroxide 2N | q.s. |
| Water | ad 1.00 ml |
| α-tocopherol | 0.250 mg |
| Na-citrate | 0.250 mg |
| Ascorbyl Palmitate | 0.250 mg |

Manufacturing method

Tiagabine hydrochloride, Na-citrate and the antioxidants are mixed in a flask with water at room temperature by stirring until the substance is soluted (approximately five minutes). While stirring the carbomer is added little by little. To make optimal viscosity sodium hydroxide is added while stirring for five minutes.

The gel is used for dermal, vaginal or rectal administration.

EXAMPLE 10
Gel containing tiagabine hydrochloride

| Composition: | |
|---|---|
| Tiagabine hydrochloride | 1.14 mg |
| Carbomer 940 | 5.00 mg |
| Sodium hydroxide 2N | q.s. |
| Water | ad 1.00 ml |
| α-tocopherol | 0.250 mg |
| Ascorbyl Palmitate | 0.250 mg |
| EDTA (Disodium Edetate) | 0.500 mg |

Manufacturing method

Tiagabine hydrochloride, the antioxidants and chelating agent are mixed in a flask with water at room temperature by stirring until the substance is soluted (approximately five minutes). While stirring the carbomer is added little by little. To make optimal viscosity sodium hydroxide was added while stirring for five minutes.

The gel is used for dermal, vaginal or rectal administration.

EXAMPLE 11
Influence of metal ions, chelator and antioxidants on Tiagabine hydrochloride stability in solutions Introduction Poor stability of drugs in dosage forms is often detected after storage for several months. On this background a model for fast evaluation of the effect of different excipients was set up.

Introductory studies showed that the model substance selected for the work ($C_{20}H_{26}NO_2S_2Cl$, Tiagabine hydrochloride) could be oxidized. Therefore, Hydrogen Peroxide was chosen as an oxidant in order to promote the oxidation process.

Experimental Methods

Chemicals

Tiagabine hydrochloride, Lot. no. 9208L 315 (NN) was used for the experiments. All other chemicals used were of analytical grade.

Analytical Method

HPLC analyses were carried out using a Waters model 501 and 516 pumps equipped with a Waters 490 E UV-detector and a Waters 700 WISP autoinjector. The column, 125 mm/4 mm, was packed with Nucleosil $C_{18}$ (5 μm). The mobile phase was 0.1% Trifluoroacetic acid in Acetonitrile/water (35:65). Flow was 1.0 ml/min, injection volume 50 μl, ambient column temperature and detector wavelength 250 nm.

Degradation of Tiagabine Hydrochloride in Reference Solutions

Solutions of tiagabine hydrochloride (100 μg/ml (0.2 mol/ml), containing 60% v/v ethanol in water, was investigated. 1 % v/v Hydrogene Peroxide was added to the solution in order to initiate the degradation of tiagabine hydrochloride. The HPLC-vials were tightly closed, and the degradation of tiagabine hydrochloride was followed at Room Temperature or at 50° C. At appropriate intervals injections were performed for HPLC quantification.

Degradation of Tiagabine Hydrochloride in Presence of Metal Ions±Chelator

In some experiments metal ions were added to the reference solutions in order to study the possibility of the metal ions in catalyzing the degradation of tiagabine hydrochloride. Amounts of metal ions corresponding to 35 ppm (~0.6 μmol/ml) of the cations $Cr^{2+}$, $Fe^{3+}$, $Zn^{2+}$, $Ni^{2+}$, $Mg^{2+}$, $Cu^{2+}$ or $CO^{2+}$ were added.

In other experiments the chelator 250 μg/ml (~0.9 μmol/ml) Sodium Citrate were added in order to prevent the catalyzing effect of the metal ions.

Degradation of Tiagabine Hydrochloride in Presence of Antioxidants

Addition of antioxidants to the reference solutions were performed in order to prevent the degradation of tiagabine hydrochloride. The concentrations of antioxidants chosen were as high as possible in the ethanol-water medium. The antioxidants were tested in the tiagabine hydrochloride solutions alone or in combination with other antioxidants.

Calculations

The degradation kinetics followed in all cases a zero order kinetics and consequently the rate constants $k_{abs}$ were calculated as the slope of the curve representing the decrease of tiagabine hydrochloride as function of time.

Results and Discussion

Degradation of Tiagabine Hydrochloride in Presence of Metal Ions ±Chelator

The values given in Table 2 shows the observed 0. order rate constants ($k_{obs}$) for degradation of tiagabine hydrochloride in solutions. $Fe^{3+}$ and $Cr^{2+}$ catalyzed the degradation of tiagabine hydrochloride, while $Zn^{2+}$ or $Ni^{2+}$ did not have any remarkable effect on the degradation process. The experiment showed that the catalyzing effect of $Cr^{2+}$ and $Fe^{3+}$ was reduced by addition of Sodium Citrate.

TABLE 2

Degradation of 100 μg/ml tiagabine hydrochloride, in 1% Hydrogen Peroxide and 60% Ethanol/Water by Adding of 35 ppm Metal Ions, RT

| | $K_{obs}$ (μg · ml$^{-1}$ · h$^{-1}$) | $K_{obs}$ (μg · ml$^{-1}$ · h$^{-1}$) + Sodium Citrate |
|---|---|---|
| Reference | | −0.1 |
| Metal ion: | | |
| $Cr^{2+}$ | −8.8 | −1.0 |
| $Fe^{3+}$ | −6.1 | −2.0 |
| $Ni^{2+}$ | −0.2 | −0.1 |
| $Zn^{2+}$ | −0.7 | |

Addition of $Cu^{2+}$ or $Co^{2+}$ was not investigated as these ions caused precipitations in the solutions.

Degradation of Tiagabine Hydrochloride in Presence of Antioxidants

Table 3 shows the observed O. order rate constants for degradation of tiagabine hydrochloride in solutions containing various antioxidants. It was chosen to study the effect of a combination of BHT, BHA and PG, because the three substances are known to have a synergistic antioxidant effect in food (Ref. 1).

The antioxidant effect of α-Tocopherol was superior to the antioxidant effect of Ascorbic Acid and "BHT, BHA and PG". The presence of Sodium Bisulfite reduced the stability of tiagabine hydrochloride in solutions.

TABLE 3

Degradation of 100 μg/ml (0.2 μmol/ml) Tiagabine Hydrochloride, in 1% Hydrogen Peroxide and 60% Ethanol/Water by Adding of Antioxidants, 50° C.

|  | μmol/ml | $K_{obs}$ ($\mu g \cdot ml^{-1} \cdot h^{-1}$) |
|---|---|---|
| Refrence |  | −0.12 |
| BHT | 0.45 |  |
| BHA | 0.55 | −0.05 |
| PG | 0.47 |  |
| α-tocopherol | 0.53 | −0.08 |
| Ascorbic Acid | 14.0 | −0.11 |
| Sodium Bisulphite | 14.0 | −0.34 |
| BHT | 0.45 |  |
| BHA | 0.55 | −0.09 |
| PG | 0.47 |  |
| Ascorbic Acid | 14.0 |  |
| α-tocopherol | 0.53 | Stable during testing |
| Ascorbyl Palmitate | 0.60 |  |

Combinations of the water soluble and the lipid soluble antioxidants did not improve the stability of tiagabine hydrochloride. The combination of α-Tocopherol and Ascorbyl Palmitate made the tiagabine hydrochloride stable during the testing period. The synergistic effect of the two antioxidants is known from other systems (Ref. 2).

Conclusion

A model was set up for an evaluation within 24 hours of the effect of different metal ions, chelator and antioxidants on the stability of tiagabine hydrochloride in solutions.

The study indicates that adding of Sodium Citrate as Chelator and α-Tocopherol & Ascorbyl Palmitate as antioxidants to tiagabine hydrochloride in a relevant dosage form would increase the stability.

Initiating the formulation work of tiagabine hydrochloride in a relevant dosage form, a model is available for rapid screening of the influence of chelators and antioxidants on the stability of tiagabine hydrochloride.

REFERENCES

[1] T. E. Furis. Handbook of Food Additives. 2nd Edition. Volume I. CRC Press.
[2] Marinova & Yanishlievd. Fat Sci. Technol. 94. Jahrgang no. 12. 1992. Page 448–452.

EXAMPLE 12

Tablets containing 0.04%, 0.4% and 1.0% per weight of tablet gross mass (320 mg) of α-tocopherol and propyl gallate, resp. where prepared as described in Example 1. The stability of the tablets were tested by storage at 40° C. and 75% RH. Results are shown in Table 4, wherein degradation products are expressed as in table 1.

TABLE 4

Sum of Degradation Products in Tablets after Storage at 40° C./75% RH

| Antioxidant | Concentration % | 1 Month | 3 Months |
|---|---|---|---|
| α-Tocopherol | 0.04 | 0.5 | 2.2 |
|  | 0.4 | 0.3 | 1.1 |
|  | 1.0 | 0.3 | 1.3 |
| Propyl gallate | 0.04 | 0.4 | 1.5 |
|  | 0.4 | 1.2 | 4.1 |
|  | 1.0 | 1.1 | 3.9 |

We claim:

1. A pharmaceutical composition comprising
    (a) tiagabine or a pharmaceuticaly acceptable salt thereof,
    (b) ascorbic acid in an amount sufficient to stabilize tiagabine or its pharmaceutically acceptable salt and
    (c) a pharmaceutically acceptable carrier.
2. The composition according to claim 1, wherein the antioxidant is in the form of a powder.
3. The composition according to claim 1, wherein the amount of ascorbic acid is from 5–25 parts by weight per 100 parts of tiagabine hydrochloride.
4. A process for the preparation of the composition according to claim 1, which comprises forming a mixture of:
    (a) tiagabine or a pharmaceutically acceptable salt thereof,
    (b) ascorbic acid and
    (c) a pharmaceutically acceptable carrier.
5. The process according to claim 4 which further comprises carrying out a melt granulation of the mixture of tiagabine or a pharmaceutically acceptable salt thereof, ascorbic acid and a pharmaceutically acceptable carrier.
6. The process according to claim 4, wherein said process is carried out at low water vapor pressure and low oxygen pressure.
7. A pharmaceutical composition comprising
    (a) tiagabine or a pharmaceuticaly acceptable salt thereof,
    (b) a mixture of alpha-tocopherol and ascorbyl palmitate in an amount sufficient to stabilize tiagabine or its pharmaceutically acceptable salt and
    (c) a pharmaceutically acceptable carrier.
8. The composition according to claim 7, wherein the antioxidant is in the form of a powder.
9. The composition according to claim 7, wherein the amount of alpha-tocopherol and ascorbyl palmitate is from 5–25 parts by weight per 100 parts of tiagabine hydrochloride.
10. A process for the preparation of the composition according to claim 7, which comprises forming a mixture of:
    (a) tiagabine or a pharmaceutically acceptable salt thereof,
    (b) alpha-tocopherol and ascorbyl palmitate and
    (c) a pharmaceutically acceptable carrier.
11. The process according to claim 10, which further comprises carrying out a melt granulation of the mixture of tiagabine or a pharmaceutically acceptable salt thereof, alpha-tocopherol and ascorbyl palmitate and a pharmaceutically acceptable carrier.
12. The process according to claim 10, wherein said process is carried out at low water vapor pressure and low oxygen pressure.

* * * * *